United States Patent [19]

Junghans

[11] Patent Number: 5,703,261
[45] Date of Patent: Dec. 30, 1997

[54] PROCESS FOR THE PRODUCTION OF SULFURIC ACID SEMI-ESTERS

[75] Inventor: Klaus Junghans, Berlin, Germany

[73] Assignee: Schering Aktiengesellschaft, Berlin, Germany

[21] Appl. No.: 624,591

[22] PCT Filed: Oct. 6, 1994

[86] PCT No.: PCT/EP94/03296

§ 371 Date: Jul. 10, 1996

§ 102(e) Date: Jul. 10, 1996

[87] PCT Pub. No.: WO95/10528

PCT Pub. Date: Apr. 20, 1995

[30] Foreign Application Priority Data

Oct. 9, 1993 [DE] Germany .................. 43 34 823.8

[51] Int. Cl.$^6$ ........................................ C07C 305/00
[52] U.S. Cl. ........................................... 558/38
[58] Field of Search ................................. 558/38

[56] References Cited

FOREIGN PATENT DOCUMENTS

| 0010056 | 4/1980 | European Pat. Off. |
| 9317036 | 9/1993 | WIPO . |

Primary Examiner—Joseph Conrad
Attorney, Agent, or Firm—Millen, White, Zelano, & Branigan, P.C.

[57] ABSTRACT

The invention relates to a process for the production of sulfuric acid semi-esters of general formula I $$RO-SO_2-OH \quad (I),$$

in which

R represents an organic radical, from hydroxy compounds of general formula II $$R-OH \quad (II),$$

in which

R has the same meaning as in formula I, characterized in that the latter is reacted in an inert solvent with a disulfuric acid salt of general formula III $$O(SO_2OX)_2 \quad (III),$$

in which

X symbolizes an alkali metal atom.

3 Claims, No Drawings

PROCESS FOR THE PRODUCTION OF SULFURIC ACID SEMI-ESTERS

The invention relates to a process for the production of sulfuric acid semi-esters of general formula I

in which

R represents an organic radical, from hydroxy compounds of general formula II

in which

R has the same meaning as in formula I.

Many such processes that are referred to as sulfation are already known (Römpp Chemie Lexikon 8th Ed., 1979, p. 4045—Frankch Publishing House, DE Stuttgart—and 9th Ed. 1992, p. 4376—Georg Thieme Verlag, Stuttgart and New York). In this known process, sulfuric acid, oleum, chlorosulfonic acid, amidosulfonic acid or sulfur trioxide are used as sulfation reagents. The sulfating reagent that is probably used most often in the case of complex hydroxy compounds is the pyridine-sulfur trioxide complex (Luis Fieser and Mary Fieser; Reagents for Organic Synthesis, John Wiley and Sons Inc., New York et al. Vol. 1, 1967, p. 127, Vol. 2, 1969, p. 393, Vol. 3, 1972, p. 275, Vol. 4, 1974, p. 473 and Vol. 9, 1981, p. 396), with whose aid, i.a., sulfuric acid semi-esters have been produced from aliphatic alcohols, from phenols, from hydroxy steroids, from carbohydrates, or from heterocyclene that contains hydroxyl groups.

This reagent, however, has not only the drawback that when it is used, considerable amounts of undesirable by-products are often formed. Even more serious is the fact that the production of the pyridine-sulfur trioxide complex itself takes place in an unusually strong exothermic reaction, which requires extremely intense and thus expensive cooling, which is quite problematic and also dangerous, especially in the case of reactions on an industrial scale. In addition, an environmentally acceptable process for disposal of the sulfuric acid that accumulates in the working-up of the reaction and waste water that contains pyridine can be implemented only at considerable expense.

It has now been found that it is possible, surprisingly enough, to produce the sulfuric acid semi-esters of general formula I from the hydroxy compounds of general formula II, by reacting the latter in an inert solvent with a disulfuric acid salt of general formula III

in which

X symbolizes an alkali metal atom.

This reaction should very probably be just as universally applicable as the sulfation of hydroxy compounds with the pyridine-sulfur trioxide complex, but to date only those hydroxy compounds of general formula II, in which radical R represents a steroid radical, have been reacted within the scope of these studies.

From the standpoint of industrial applicability, interest is focused mainly on the production of those sulfuric acid semi-esters that are referred to as conjugated estrogens (conjugated estrogens are contained, for example, in the Premarin[(R)] tablets of the Ayerst Labs. company, New York; detailed data on the subject of conjugated estrogens are found in, for example, the publications Pharmacopeial Forum, May, June 1991, pp. 1951–1962 and Journal of Chromatography 224, 1981, 355–370 as well as 234, 1982, 234–239).

These pharmacologically effective conjugated estrogens that include a few intermediate products for their production are characterized by general formula Ia

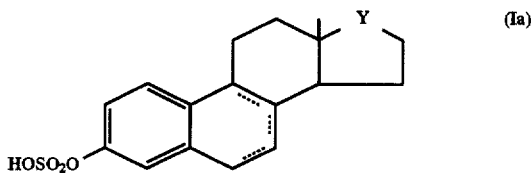

in which the three bonds characterized by ...... symbolize three single bonds, two single bonds and a double bond, or two conjugated double bonds, and Y represents a carbonyl group, a hydroxymethylene group, an acyloxymethylene group with up to 8 carbon atoms in the acyl radical, or a benzyloxymethylene group.

The conjugated estrogens of general formula Ia can be produced using the process according to the invention from the corresponding hydroxy compounds of general formula IIa

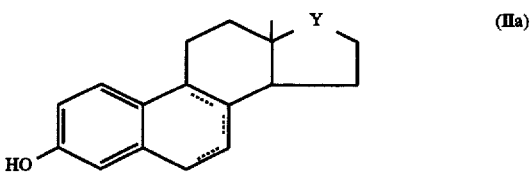

in which bonds ...... and Y have the same meanings as in formula Ia.

Only in the case of the compounds of formula IIa with Y meaning a hydroxymethylene group are just quite small yields of desired process product generally obtained, since this hydroxymethylene group is preferably converted to the sulfate ester.

For the production of conjugated estrogens of general formula Ia with a free 17α- or 17β-hydroxy group, in most cases the first step in achieving good yields is to take hydroxy compounds of formula IIa; their 17-hydroxy groups are esterified or etherified with a benzyl group, the latter are converted to the corresponding conjugated estrogens of general formula Ia, and the protective groups are removed in a known way.

The process itself according to the invention can be implemented in a simple way. The hydroxy compound of general formula I is dissolved or suspended in an inert solvent and mixed with 1.05–1.5 mol of disulfate of formula III, and the reaction mixture is stored at a temperature of 0° C. to 60° C. optionally while being stirred for 1 hour to 48 hours.

Suitable inert solvents are, for example, chlorinated hydrocarbons, such as dichloromethane or tetrachloroethane, ethers such as diisopropyl ether, dibutyl ether, 1,2-dimethoxyethane, tetrahydrofuran or dioxane, or dipolar aprotic solvents such as dimethylformamide, N-methylacetamide, dimethyl sulfoxide or hexamethylphosphoric triamide.

Suitable disulfates are especially disodium or dipotassium disulfate.

The working-up of the reaction mixture can be carried out in the same way as is done in the sulfation of hydroxy compounds with the pyridine-sulfur trioxide complex.

The following embodiments are used to explain the process according to the invention in more detail.

EXAMPLE 1

0.5 g of 3-hydroxy-estra-1,3,5(10)-trien-17-one and 0.5 g of sodium disulfate are mixed with 2 ml of dimethylformamide and 3 ml of tetrahydrofuran and allowed to stand for 30 hours at room temperature. Then, 5 ml of a 1N aqueous sodium carbonate solution is added to the reaction mixture, it is filtered, and the filtrate is concentrated by evaporation in a vacuum. The residue is taken up in 50 ml of water, filtered with activated carbon, and the filtrate is freeze-dried. 0.6 g of the sodium salt of 3-hydroxy-estra-1,3,5(10)-trien-17-one-3-hemisulfate is obtained as colorless powder with a melting point of 270°–277° C.

$[\alpha]_D$=+81.2° (methanol).

EXAMPLE 2

0.5 g of 17α-acetoxy-estra-1,3,5(10)-trien-3-ol in 2 ml of dimethylformamide is mixed in 0.5 g of sodium disulfate and allowed to stand for 24 hours at room temperature. Then, the reaction mixture is mixed with 10 ml of a 1N aqueous sodium carbonate solution, and after 2 hours it is poured over a reversed-phase chromatography column (J. Chem. Soc., Perkin Trans. I, 1987, 1339f). The latter is washed with 20 ml of distilled water and eluted with methanol, the eluate is concentrated by evaporation in a vacuum, and 0.5 g of the sodium salt of estra-1,3,5(10)-triene-3,17β-diol-3-hydrogen sulfate with a melting point of 156°–158° C. (decomposition) is obtained.

$[\alpha]_D$=+40.3° (methanol).

EXAMPLE 3

0.5 g of 17α-acetoxy-estra-1,3,5(10),7-tetraen-3-ol is mixed with 3 ml of dimethylformamide and 0.5 g of sodium disulfate and allowed to stand for 30 hours at room temperature. The reaction mixture is neutralized with aqueous sodium bicarbonate solution, and it is concentrated by evaporation in a vacuum. The residue is mixed with 7 ml of 1N aqueous sodium hydroxide solution, allowed to stand for 1.5 hours at room temperature, and neutralized with 1N aqueous sulfuric acid. Then, the reaction mixture is mixed with 20 ml of isopropanol, filtered, and the filtrate is concentrated by evaporation in a vacuum. The residue is dissolved in 25 ml of water of 50° C. and filtered with activated carbon, and the filtrate is concentrated by evaporation in a vacuum. 0.4 g of the sodium salt of estra-1,3,5 (10),7-tetraene-3,17α-diol-3-hemisulfate is obtained as a beige powder with a melting point of 155°–157° C. (decomposition).

$[\alpha]_D$=+155° (methanol).

EXAMPLE 4

0.5 g of 17α-acetoxy-estra-1,3,5(10),6,8-pentaen-3-ol is mixed with 2 ml of dimethylformamide and 0.5 g of sodium disulfate and stirred for 20 hours at 20° C. Then, the reaction mixture is neutralized with 5 ml of aqueous sodium bicarbonate solution, and it is evaporated to the dry state in a vacuum. The residue is taken up in 15 ml of aqueous sodium hydroxide solution, allowed to stand for 24 hours, and neutralized with acetic acid. The reaction mixture is placed on a reversed-phase chromatography column, washed with water, and eluted with methanol. The eluate is concentrated by evaporation in a vacuum, and 0.4 g of estra-1,3,5(10),6,8-pentaen-3,17α-diol-3-hemisulfate-sodium with a melting point of 166° C. is obtained.

$[\alpha]_D$=−4.5° (methanol).

EXAMPLE 5

Under the conditions of Example 2, 0.5 g of 3-hydroxy-estra-1,3,5(10),8-tetraen-17-one is reacted with sodium disulfate and worked up, and 0.4 g of 3-hydroxy-estra-1,3,5 (10),8-tetraen-17-ene-3-hemisulfate-sodium is obtained.

EXAMPLE 6

Under the conditions of Example 2, 0.5 g of estra-1,3,5 (10),7-estratetraene-3,17β-diol is reacted with sodium disulfate and worked up, and 0.4 g of estra-1,3,5(10),7-tetraene-3,17β-diol-17-hemisulfate-sodium is obtained.

I claim:

1. Process for the production of sulfuric acid semi-esters of general formula I

in which

R represents an organic radical, from hydroxy compounds of general formula II

in which

R has the same meaning as in formula I, characterized in that the latter is reacted in an inert solvent with a disulfuric acid salt of general formula III

in which

X symbolizes an alkali metal atom.

2. Process for the production of sulfuric acid semi-esters of general formula I according to claim 1, wherein R symbolizes the radical of a hydroxy steroid.

3. Process for the production of conjugated estrogens of general formula Ia

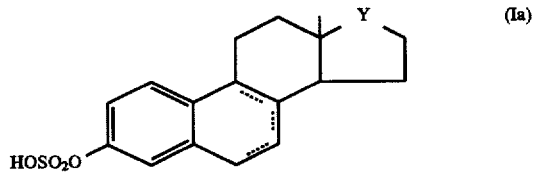

in which the three bonds characterized by ...... symbolize three single bonds, two single bonds and a double bond, or two conjugated double bonds, and Y represents a carbonyl group, a hydroxymethylene group, an acyloxymethylene group with up to 8 carbon atoms in the acyl radical or a benzyloxymethylene group, wherein hydroxy steroids of general formula IIa

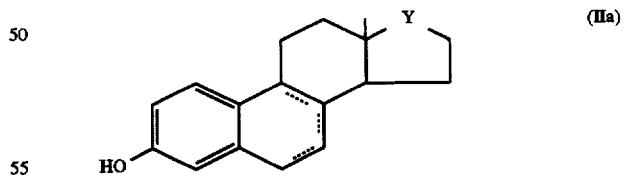

in which bonds ....... and Y have the same meanings as in formula Ia, are reacted in an inert solvent with a disulfuric acid salt of general formula III

in which

X symbolizes an alkali metal atom.

* * * * *